US012721386B2

(12) United States Patent
Takagi et al.

(10) Patent No.: US 12,721,386 B2
(45) Date of Patent: Sep. 1, 2026

(54) MASK

(71) Applicant: Murata Manufacturing Co., Ltd., Nagaokakyo (JP)

(72) Inventors: Masayoshi Takagi, Nagaokakyo (JP); Daiji Tamakura, Nagaokakyo (JP); Kenichiro Takumi, Nagaokakyo (JP); Ryosuke Ebina, Osaka (JP); Koji Takeshita, Osaka (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 695 days.

(21) Appl. No.: 17/974,715

(22) Filed: Oct. 27, 2022

(65) Prior Publication Data

US 2023/0041282 A1 Feb. 9, 2023

Related U.S. Application Data

(63) Continuation of application No. PCT/JP2021/021078, filed on Jun. 2, 2021.

(30) Foreign Application Priority Data

Jun. 3, 2020 (JP) ................................ 2020-096809

(51) Int. Cl.
*A41D 13/11* (2006.01)
*A61L 9/22* (2006.01)

(52) U.S. Cl.
CPC ........... *A41D 13/1161* (2013.01); *A61L 9/22* (2013.01); *A41D 2500/20* (2013.01); *A61L 2209/14* (2013.01)

(58) Field of Classification Search
CPC ........... A41D 13/1161; A41D 2200/20; A41D 13/1192; A61L 9/22; A62B 18/02
See application file for complete search history.

(56) References Cited

U.S. PATENT DOCUMENTS 3,974,829 A * 8/1976 Tate, Jr. ............ A41D 13/1115 128/201.17
2002/0046754 A1 4/2002 Baumann et al.
2010/0221307 A1 9/2010 Matsushita et al.
2011/0057127 A1* 3/2011 Slinkard ............... A41D 31/26 174/388
2011/0232653 A1 9/2011 Imashiro et al.
2013/0291878 A1 11/2013 Takayama et al.
(Continued)

FOREIGN PATENT DOCUMENTS

EP 3 536 838 B1 * 1/2025 .......... A41D 30/857
JP 2002506663 A 3/2002
(Continued)

OTHER PUBLICATIONS

International Search Report in PCT/JP2021/021078, mailed Aug. 17, 2021, 3 pages.

*Primary Examiner* — Camtu T Nguyen
(74) *Attorney, Agent, or Firm* — ArentFox Schiff LLP

(57) ABSTRACT

A mask for covering at least a nostril and a mouth of a wearer. The mask includes a main body portion and an ear hooking portion attached to the main body portion. At least a part of the main body portion has a sheet-like piezoelectric portion, and the piezoelectric portion includes a yarn formed of an electric field forming filament.

16 Claims, 12 Drawing Sheets

(56) References Cited

U.S. PATENT DOCUMENTS

| | | | | |
|---|---|---|---|---|
| 2014/0165515 | A1* | 6/2014 | Matsuda | D04H 3/016 55/482 |
| 2019/0038787 | A1 | 2/2019 | Ando | |
| 2019/0078239 | A1* | 3/2019 | Ando | D02G 3/441 |
| 2019/0336895 | A1* | 11/2019 | Inoue | D02G 3/449 |
| 2020/0157709 | A1* | 5/2020 | Kanematsu | H10N 30/702 |
| 2020/0315266 | A1* | 10/2020 | McMahon | A41D 13/1161 |

FOREIGN PATENT DOCUMENTS

| | | | | |
|---|---|---|---|---|
| JP | 2006503665 | A | * | 2/2006 |
| JP | 2008188082 | A | | 8/2008 |
| JP | 2010030983 | A | | 2/2010 |
| JP | 2012075802 | A | | 4/2012 |
| JP | 6428979 | B1 | | 11/2018 |
| WO | 2011/026515 | A1 | | 3/2011 |
| WO | 2012091087 | A1 | | 7/2012 |
| WO | 2018/117004 | A1 | | 6/2018 |
| WO | 2018151058 | A1 | | 8/2018 |
| WO | 2019077957 | A1 | | 4/2019 |

* cited by examiner

Fig. 12A
Fig. 12B
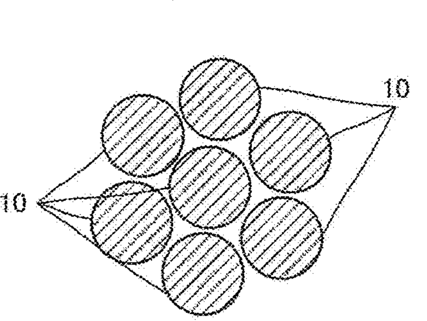
Fig. 12C
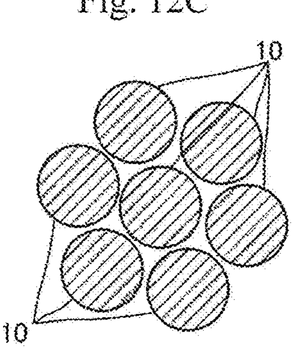

MASK

CROSS REFERENCE TO RELATED APPLICATIONS

The present application is a continuation of International application No. PCT/JP2021/021078, filed Jun. 2, 2021, which claims priority to Japanese Patent Application No. 2020-096809, filed Jun. 3, 2020, the entire contents of each of which are incorporated herein by reference.

FIELD OF THE INVENTION

The present invention relates to a mask. More specifically, the present invention relates to a mask for covering at least a nostril and a mouth.

BACKGROUND OF THE INVENTION

Conventionally, masks having functions such as an antibacterial property have been developed. For example, Patent Document 1 discloses a mask using an inorganic porous material such as zeolite. Patent Document 2 discloses a mask using an antiviral agent. Patent Document 3 discloses a mask using a functional substance such as catechin polyphenols. Patent Document 4 discloses a mask using an electretized nonwoven fabric. Patent Document 5 discloses a multilayer structure mask using piezoelectric fibers.

Patent Document 1: JP-A-2008-188082
Patent Document 2: JP-A-2010-30983
Patent Document 3: WO 2012/091087
Patent Document 4: WO 2018/151058
Patent Document 5: WO 2019/077957

SUMMARY OF THE INVENTION

The inventors of the present application have noticed that known masks have problems to be overcome, and have found the need to take measures therefor. Specifically, the inventors of the present application have found that there are the following problems.

Conventionally, a mask using a functional substance such as an inorganic porous material, an antiviral agent, and catechin polyphenols has been developed (refer to Patent Documents 1 to 3). However, since a mask usually covers a nostril or a mouth, it cannot be said that the safety is sufficient when considering that such a drug or substance is mixed into a human body. In addition, in a mask using an electretized nonwoven fabric (refer to Patent Document 4), there are problems such as a problem that charge disappears over time with use of the mask and collection efficiency decreases, and a problem that charge disappears due to washing and the mask cannot be repeatedly used, and there is room for further improvement. In addition, also in a mask using piezoelectric fibers (refer to Patent Document 5), there is room for further improvement such as improvement of an antibacterial effect due to the piezoelectricity thereof.

The present invention has been made in view of such problems. That is, a main object of the present invention is to provide a mask with improved safety and function.

The inventors of the present invention have attempted to solve the above problems by addressing the problems in a new direction instead of addressing the problems in an extension of the conventional technique. As a result, the inventors of the present invention have reached the invention of a mask that has achieved the above main object.

The inventors of the present application first focused on the fact that a "yarn formed of an electric field forming filament" generates a potential by receiving energy (for example, tension, stress, or the like) from the outside and forming an electric field, and for example, an antibacterial action or the like is exerted by such a potential.

As a result of intensive studies by the inventors of the present application, for example, in a mask made of cloth prepared using such a yarn, it has been found that by improving the elasticity of a desired site where an electric field and/or a potential are intended to be generated, or by reducing the elasticity of a site where an electric field and/or a potential are not intended to be generated, tension and/or stress applied to the yarn are concentrated and the electric field and/or the potential are intensively generated at a desired site where the electric field and/or the potential are intended to be generated, and thus an effect or function such as antibacterial property and/or antiviral property can be improved. In addition, according to the studies of the inventors of the present application, it has also been found that a mask that exhibits an effect such as the antibacterial property by generating such an electric field and/or potential can be used more safely since it is not necessary to add a drug such as zeolite or an antiviral agent unlike the mask in the prior art.

Based on such findings, the present invention provides a mask for covering at least a nostril and a mouth of a wearer, the mask including a main body portion and an ear hooking portion attached to the main body portion, wherein at least a part of the main body portion includes a sheet-like piezoelectric portion, and the piezoelectric portion includes a yarn formed of an electric field forming filament. More specifically, there is provided a mask in which a main body portion of the mask includes a piezoelectric region including a piezoelectric portion and a non-piezoelectric region, and the piezoelectric region expands and contracts more than the non-piezoelectric region.

In the present invention, a mask with further improved safety and function is obtained. More specifically, a safer mask with improved functions such as antibacterial property and/or antiviral property may be obtained. Note that the effects described in the present specification are merely examples and are not limited, and additional effects may be provided.

BRIEF DESCRIPTION OF THE DRAWINGS

FIG. 12A is a diagram illustrating a configuration of a yarn 1 (S yarn), FIG. 12B is a sectional view taken along line A-A of FIG. 12A, and FIG. 12C is a sectional view taken along line B-B of FIG. 12A.

FIG. 14A is a diagram illustrating a configuration of a yarn 2 (Z yarn), FIG. 14B is a sectional view taken along line A-A of FIG. 14A, and FIG. 14C is a sectional view taken along line B-B of FIG. 14A.

DESCRIPTION OF PREFERRED EMBODIMENTS OF THE INVENTION

The present invention relates to a mask for covering at least a nostril and a mouth, as illustrated FIG. 1 (hereinafter, the mask may be referred to as a "mask of the present disclosure" or may be abbreviated and simply called "mask"). Specifically, the mask of the present disclosure includes a "main body portion" and an "ear hooking portion", wherein at least a part of the main body portion includes a sheet-like "piezoelectric portion", and the piezoelectric portion includes a "yarn formed of an electric field forming filament" (for example, yarns illustrated in FIGS. 12A to 15). More specifically, in the mask of the present disclosure, the main body portion of the mask includes a "piezoelectric region" including the "piezoelectric portion" and a "non-piezoelectric region", and the "piezoelectric region" "expands and contracts" more than the "non-piezoelectric region" (refer to, for example, the schematic view illustrated in FIGS. 3A to 3C).

Hereinafter, the mask of the present disclosure will be described in detail based on a structure thereof.

Mask of the Present Disclosure

Figure 1:
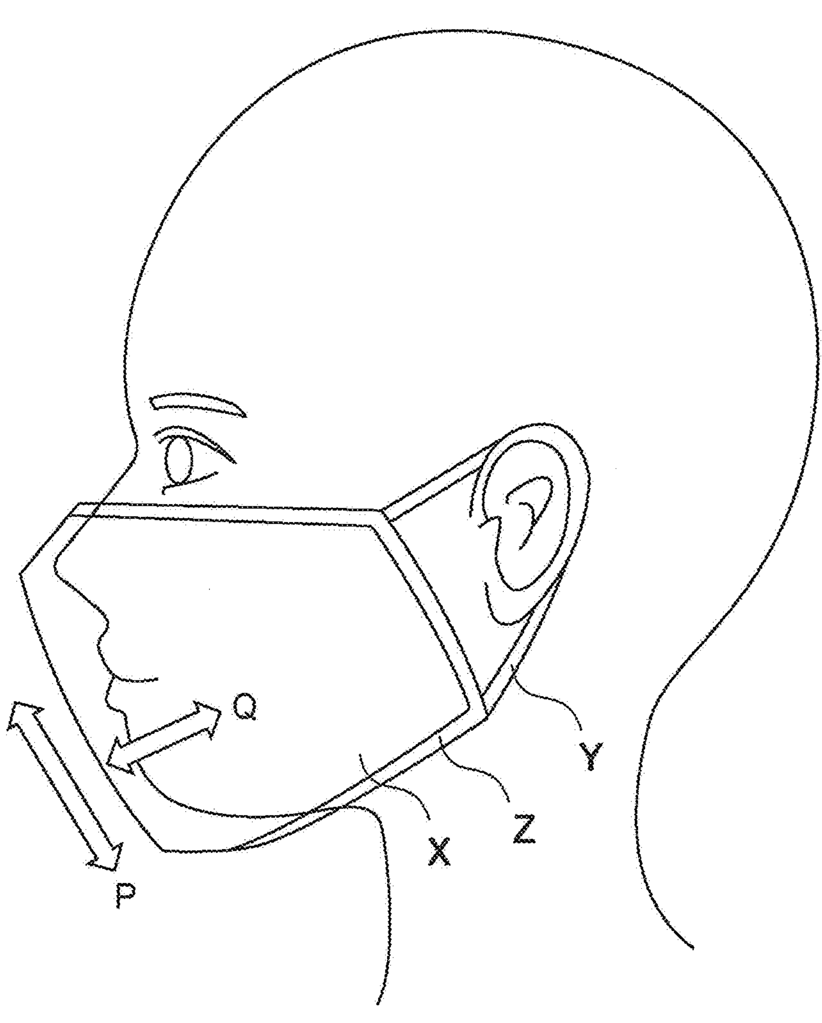
FIG. 1 is a schematic view schematically illustrating a state in which a mask according to an embodiment of the present invention is worn on a face.

The mask of the present disclosure has at least a "main body portion" and an "ear hooking portion", and is configured to cover at least a nostril and a mouth by being worn on a human's face, for example, as illustrated in FIG. 1.

In the present disclosure, the "main body portion" of the mask means a portion or member that can cover at least the nostril and the mouth by being worn on the human's face, for example, as indicated by reference numeral X in FIG. 1. For example, as illustrated in FIG. 1, the main body portion X may have a three-dimensional shape (3D shape) spreading three-dimensionally, or may have a planar shape (2D shape) spreading two-dimensionally. The dimension of the main body portion X is not particularly limited as long as the main body portion X can cover at least the nostril and the mouth as illustrated in FIG. 1, for example, and it is preferable that the main body portion X has a dimension capable of covering even the tip of the nose, a part of the ridge of the nose, and the chin as illustrated in FIG. 1, for example.

In the mask of the present disclosure, "at least a part" of the main body portion includes a sheet-like "piezoelectric portion", and the piezoelectric portion includes a "yarn" (for example, yarns illustrated in FIGS. 12A to 15) including an "electric field forming filament" to be described in detail below.

As described in detail below, the "electric field forming filament" can generate an electric field and/or a potential (or a charge), for example, when the energy (for example, tension, stress, or the like) is applied from the outside, so that an effect such as antibacterial property and/or antiviral property can be exhibited due to the electric field and/or the potential generated in this manner.

The "electric field forming filament" may be referred to as a "potential generating filament" since it can generate a charge and generate a potential by energy from the outside (hereinafter, it may be referred to as "electric field forming fiber" or "potential generating fiber" or "charge generating fiber" or "charge generating filament"). The term "potential generating filament" can be used substantially synonymously with "electric field forming filament".

Examples of the "energy from the outside" include a force from the outside (hereinafter, it may be referred to as an "external force"), specifically a force that causes deformation or strain in the yarn or filament and/or a force applied in the axial direction of the yarn or filament, more specifically, a tension (for example, tensile force in the axial direction of the yarn or filament) and/or a stress or a strain force (tensile stress or tensile strain on the yarn or filament) and/or a force applied in the transverse direction of the yarn or filament.

In the mask of the present disclosure, by using a piezoelectric portion having a "yarn" formed of such an "electric field forming filament", preferably a piezoelectric portion that can be configured to include a "yarn formed of an electric field forming filament", for "at least a part" of the main body portion (refer to, for example, FIGS. 3A to 3C), effects such as antibacterial property and/or antiviral property can be more effectively exhibited by application of energy from the outside than before. For example, as illustrated in FIG. 1, when a force is applied to the main body portion X in an "vertical direction" (for example, a direction indicated by an arrow P) and/or a "horizontal direction" (for example, a direction indicated by an arrow Q), specifically, when the force is applied due to movement of the mouth or the like, more specifically, when the force is applied due to utterance, chewing of food such as gum, or a physiological phenomenon such as cough or sneezing, it is possible to achieve effects such as antibacterial property and/or antiviral property more effectively than before. Here, the "vertical direction" of the main body portion means, for example, a vertical direction when a mask is worn on the face and viewed from the front, more specifically, a direction along the ridge of the nose or a direction perpendicular to the lip (direction indicated by the arrow P in FIGS. 2A and 2B, particularly FIG. 2B, for example). Here, the "horizontal direction" of the main body portion means, for example, a horizontal direction when a mask is worn on the face and viewed from the front, more specifically, a direction perpendicular to the ridge of the nose or a direction along the lip (direction indicated by the arrow Q in FIGS. 2A and 2B, particularly FIG. 2B, for example).

In the present disclosure, the "piezoelectric portion" means a portion or a member that can be mainly formed of a "yarn formed of an electric field forming filament" to be described in detail below. More specifically, it means a sheet-like portion or member that can generate an electric field and/or a potential (or charge) on the surface thereof by applying energy (for example, tension, stress, or the like) from the outside. More specifically, it means a knitted fabric (for example, a knit), a woven fabric (for example, a woven fabric formed of stretch yarns having a spandex score, preferably a woven fabric having stretchability), a nonwoven fabric (for example, needle punching or spunbonding), or the like that can be constituted by the "yarn formed of an electric field forming filament".

In the present disclosure, the "ear hooking portion" of the mask means, for example, a string-like or band-like portion or member indicated by reference numeral sign Y that can extend from the main body portion and hang on the ear as illustrated in FIG. 1. A material constituting the ear hooking portion is not particularly limited. Such an ear hooking portion can be made of, for example, cloth (knitted fabric, woven fabric, nonwoven fabric, and the like) or string (strings made of yarn, leather, rubber, and the like, and the like). More specifically, the ear hooking portion can be made of a binder tape, a microfiber cloth, or the like. Such an ear hooking portion may or may not have elasticity. Such an ear hooking portion preferably has low elasticity in order to concentrate external energy on the piezoelectric portion that can constitute at least a part of the main body portion. Here, the "low elasticity" of the ear hooking portion means that the elasticity of the ear hooking portion is relatively low as compared with the elasticity of the piezoelectric portion that can constitute the main body portion. The ear hooking portion can be installed to fix the main body portion of the mask at least at a position covering the nostril and the mouth, and may not be a structure limited to hanging on the ear. For example, a headrest structure in which the left and right sides of the main body portion are connected to support at the back of the head may be used.

The mask of the present disclosure may have an "edge portion" as necessary. In the present disclosure, the "edge portion" means a portion or member that can be disposed in the periphery of the main body portion, and means a portion or member that can cover the periphery of the main body portion, for example, as indicated by reference numeral Z in FIGS. 1 and 2A-2B. Such an edge portion may cover the entire periphery of the main body portion or only a portion of the periphery of the main body portion. There is no particular limitation on the material that can constitute the edge portion. Such an edge portion can be made of, for example, cloth (woven fabric, knitted fabric, nonwoven fabric, and the like). More specifically, the edge portion can be made of a binder tape, a microfiber cloth, or the like. Such an edge portion may or may not have elasticity. Such an edge portion preferably has low elasticity in order to concentrate external energy on the piezoelectric portion that can constitute at least a part of the main body portion. Here, the "low elasticity" of the edge portion means that the elasticity of the edge portion is relatively low as compared with the elasticity of the piezoelectric portion that can constitute at least a part of the main body portion. In addition, by using a high friction material (or a material having a high frictional force or a friction material) for a portion (or a skin side) that can come into contact with the skin of the edge portion, deviation of the mask hardly occurs, and it is possible to concentrate external energy on the piezoelectric portion that can constitute at least a part of the main body portion. A material having a high frictional force is not particularly limited. The material having high frictional force may be, for example, a rubber material generally used for preventing slippage of clothing, an adhesive generally used for adhesive plaster or medical dressing, or a cloth-like material that can be produced from NANOFRONT (registered trademark) manufactured by TEIJIN FRONTIER Co., Ltd. Furthermore, in order to make deviation of the mask, particularly the main body portion, less likely to occur, a metal or resin wire or the like may be disposed or embedded in a portion of the edge portion that can be in contact with the tip of the nose or the ridge of the nose. Such a wire may have flexibility or may be deformable according to the unevenness of the face.

In the present disclosure, the "elasticity" generally means a property capable of repeatedly extending and contracting (also referred to as "stretchability"). The elasticity may be determined, for example, based on a test method such as "JIS L 1096 Testing methods for woven and knitted fabrics".

In the mask of the present disclosure, as described above, at least a part of the main body portion includes the piezoelectric portion, and such a main body portion preferably includes a "piezoelectric region" which may be formed of the piezoelectric portion, and a "non-piezoelectric region". The "piezoelectric region" more preferably expands and contracts or has higher elasticity than that of the "non-piezoelectric region".

In the present disclosure, the "piezoelectric region" means at least a partial region of the main body portion including the piezoelectric portion, and as described above, for example, means a region where an electric field, a potential (or charge), or the like can be generated on a surface of the main body portion when external energy (for example, tension, stress, or the like) is applied. The piezoelectric region is preferably formed of knitted fabrics (for example, a knit), woven fabrics (for example, a woven fabric made of stretch yarns having a spandex score, preferably a woven fabric having stretchability, more preferably a woven fabric having stretchability more than a non-piezoelectric region), or a nonwoven fabric of "a yarn formed of an electric field forming filament" described in detail below.

In the present disclosure, the "non-piezoelectric region" generally means other regions of the main body portion except for a region formed of the piezoelectric portion of the main body portion.

In the present disclosure, "the piezoelectric region expands and contracts more than the non-piezoelectric region" means that, for example, the "piezoelectric region" has relatively higher "elasticity" than that of the "non-piezoelectric region", or has "softness" or "flexibility". Alternatively, it means that the "non-piezoelectric region" has "elasticity" relatively lower than that of the "piezoelectric region", or has "hardness" or "rigidity".

The material that can constitute the "non-piezoelectric region" in the present disclosure can be used without particular limitation as long as the "non-piezoelectric region" is a material having relatively lower elasticity than that of the "piezoelectric region". Specifically, the material is a sheet-like material such as a woven fabric or a knitted fabric (for example, tricot). Here, the yarn used for the woven fabric or the knitted fabric may be a general natural fiber or a chemical fiber, and may be a "yarn formed of an electric field forming filament". In this case, the yarn may be a sheet having a structure organized relatively lower than that of the piezoelectric region. The non-piezoelectric region may be molded by being solidified in, for example, in a cup shape so as to have relatively lower elasticity than that of the piezoelectric region.

Figure 2A:
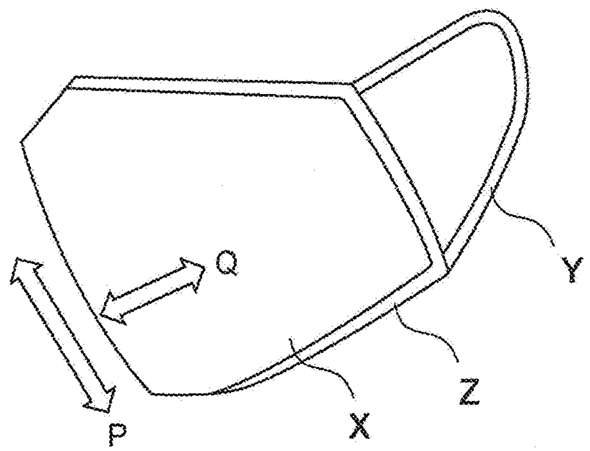
FIGS. 2A and 2B are a schematic view schematically illustrating a mask according to an embodiment of the present invention.

In the mask of the present disclosure, for example, when an external force is applied in the vertical direction indicated by the arrow P and/or the horizontal direction indicated by the arrow Q in FIG. 2A, the "piezoelectric portion" or the "piezoelectric region" included in the main body portion X can expand and contract or deform in the vertical direction and/or the horizontal direction. At this time, since the "non-piezoelectric region" has relatively lower elasticity than that of the piezoelectric region (or has lower flexibility or has hardness), the external force is more concentrated on the "piezoelectric region". As a result, an electric field and/or a potential can be more effectively generated in the "piezoelectric region", and for example, effects such as antibacterial property and antiviral property can be more remarkably exhibited. Therefore, the "piezoelectric region" is preferably disposed, for example, in a portion covering the nostril or the mouth. More specifically, in the schematic diagram schematically and formally illustrating the main body portion X of FIG. 2B in a rectangular shape, it is preferable to dispose the "piezoelectric region" in the portions b, d, e, and/or f and the like of the main body portion X capable of covering the nostril and the mouth, and it is preferable to dispose the "non-piezoelectric region" in the portions a and/or c and the like of the main body portion X.

In the main body portion of the mask of the present disclosure, the "piezoelectric region" is preferably disposed in the "lower half" of the main body portion. More specifically, as schematically and formally illustrated in FIG. 3A, the "piezoelectric region" is preferably disposed in the three portions d, e, and f of the main body portion. When the mask is worn on the face, the mouth can be entirely covered by the portions d, e, and f, particularly the portion e, where the piezoelectric region is disposed, and an electric field/potential can be generated according to the movement of the mouth (refer to FIG. 2B). At this time, the "non-piezoelectric region" is preferably disposed in the portions a, b, and c (that is, the "upper half") of the main body portion. Since the "non-piezoelectric region" exists in the "upper half" of the main body portion, the "non-piezoelectric region" has a relatively lower "elasticity" than that of the "piezoelectric region" (that is, since the "piezoelectric region" has a relatively higher "elasticity" than that of the "non-piezoelectric region"), energy from the outside can be more concentrated in the "piezoelectric region" disposed in the "lower half" of the main body portion. In particular, since the "upper half" of the main body portion is relatively or substantially fixed by such a "non-piezoelectric region", the "piezoelectric region" of the "lower half" can more effectively expand and contract in a concentrated manner in the "vertical direction (or longitudinal direction)" in accordance with the movement of the mouth. As a result, in the portions d, e, and f where the "piezoelectric region" is disposed, even if the movement of the mouth is fine, that is, even if the expansion and contraction of the piezoelectric region is fine, the electric field/potential can be concentrated and effectively generated in the "lower half" of the main body portion. For this reason, it is possible to exhibit a more improved antibacterial effect, antiviral effect, and the like with respect to the air entering and exiting the mouth.

Figure 2B:
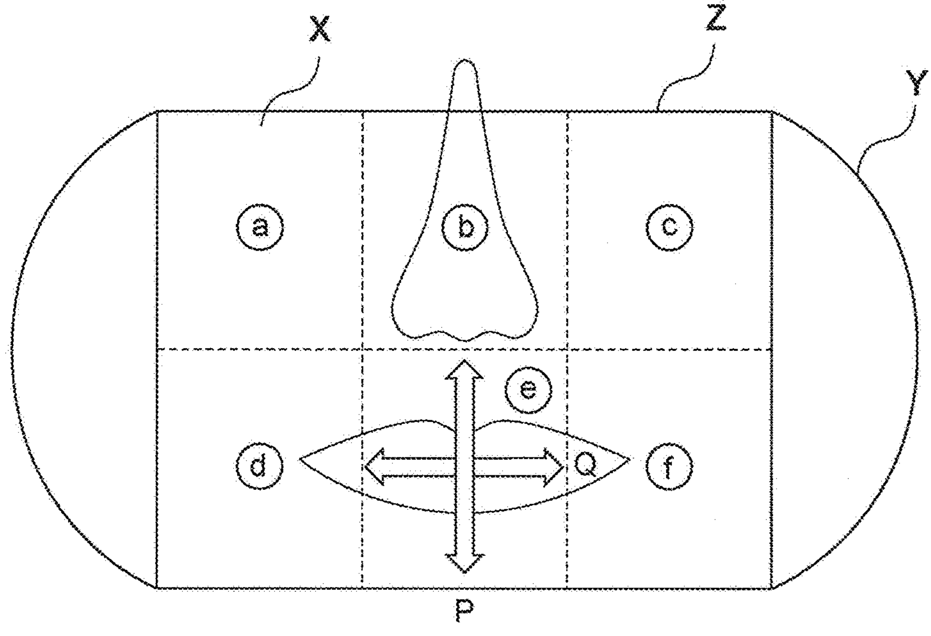
Figure 3A:
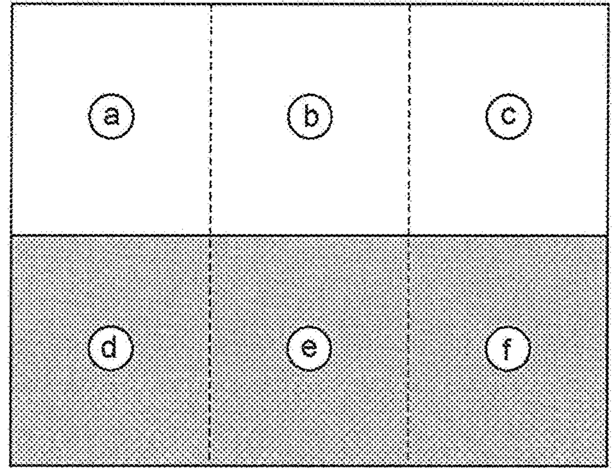
FIGS. 3A to 3C are a schematic view schematically illustrating a main body portion of a mask according to some embodiments of the present invention.
Figure 3B:
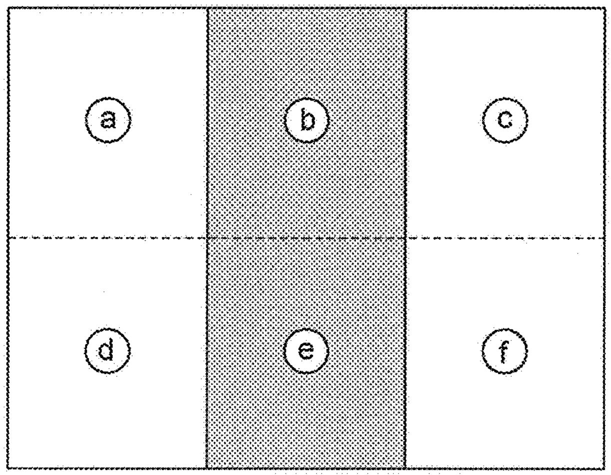
Figure 3C:
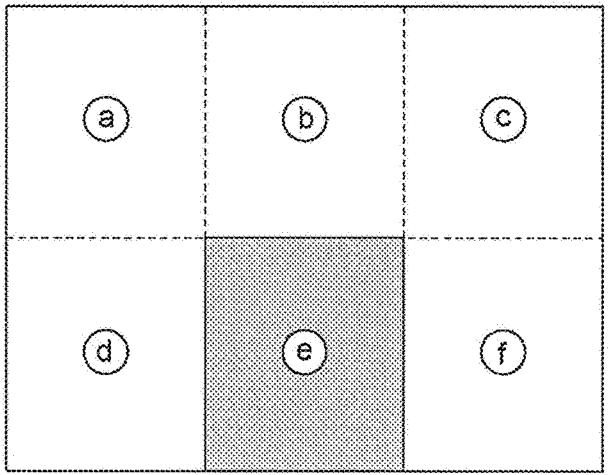

In the main body portion of the mask of the present disclosure, the "piezoelectric region" is preferably disposed in a "band shape in the vertical direction passing through the center of the main body portion" (here, the "center of the main body portion" refers to a geometric center of the main body portion, for example, an intersection of diagonal lines of a rectangle in the aspect illustrated in FIGS. 3A to 3C). More specifically, as schematically and formally illustrated in FIG. 3B, the "piezoelectric region" is preferably disposed in the two portions b and e of the main body portion. When the mask is worn on the face, the nose and the mouth can be covered in a band shape in the vertical direction (or the longitudinal direction) by the portions b and e where the piezoelectric region is disposed (refer to FIG. 2B). At this time, it is preferable that the "non-piezoelectric region" is divided and disposed in the left portions a and d and the right portions c and f (that is, "both left and right sides") of the main body portion. Since the "non-piezoelectric region" exists in the "both left and right sides" of the main body portion, the "non-piezoelectric region" has a relatively lower "elasticity" than that of the "piezoelectric region" (that is, since the "piezoelectric region" has a relatively higher "elasticity" than that of the "non-piezoelectric region"), energy from the outside can be more concentrated in the "piezoelectric region" (b, e) disposed in the "band shape in the vertical direction passing through the center of the main body portion". In particular, since both left and right sides of the main body portion are relatively or substantially fixed by the "non-piezoelectric region" (a, d and c, f), the "piezoelectric region" can more effectively expand and contract in a concentrated manner in the "vertical direction (or the longitudinal direction or the direction along the ridge of the nose)" and the "horizontal direction (or the lateral direction or the direction along the lip)" in a concentrated manner in accordance with the movement of the mouth. As a result, in the portions b and e where the "piezoelectric region" is disposed, even if the movement of the mouth is fine, that is, even if the expansion and contraction of the piezoelectric region is fine, the electric field/potential can be concentrated and effectively generated in the band-shaped portion in the vertical direction (or longitudinal direction) at the center of the main body portion. For this reason, it is possible to exhibit a more improved antibacterial effect, antiviral effect, and the like with respect to the air entering and exiting the nose and the mouth.

In the main body portion of the mask of the present disclosure, the "piezoelectric region" is preferably disposed in the "central portion of the lower half" of the main body portion (here, the "central portion" of the main body portion refers to, for example, portions b and e in the aspect illustrated in FIGS. 2B and 3B, and the "central portion of the lower half" of the main body portion refers to, for example, portion e in the aspect illustrated in FIG. 3C). More specifically, as schematically and formally illustrated in FIG. 3C, the "piezoelectric region" is preferably disposed in only the portion e of the main body portion. When the mask is worn on the face, the mouth can be mainly covered by the portion e where the piezoelectric region is disposed (refer to FIG. 2B). At this time, in the portions a to d and f of the main body portion, the "non-piezoelectric region" is preferably disposed so as to surround the portion e (that is, the "piezoelectric region"). Since the "non-piezoelectric region" (a to d and f) exists so as to surround the "piezoelectric region" (e) of the main body portion, the "non-piezoelectric region" has a relatively lower "elasticity" than that of the "piezoelectric region" (that is, since the "piezoelectric region" has a relatively higher "elasticity" than that of the "non-piezoelectric region"), energy from the outside can be more concentrated in the "piezoelectric region" (e) surrounded by the "non-piezoelectric region". In particular, since the "non-piezoelectric region" (a to d and 0 is relatively or substantially fixed, the "piezoelectric region" (e)

can more effectively expand and contract in a concentrated manner in accordance with movement of the mouth. As a result, in the "piezoelectric region" (e), even if the movement of the mouth is fine, that is, even if the expansion and contraction of the piezoelectric region is fine, the electric field/potential can be concentrated and effectively generated in the "piezoelectric region" (e). For this reason, it is possible to further improve the antibacterial effect and the antiviral effect particularly with respect to the air entering and exiting the mouth.

Here, in the aspect schematically and formally illustrated in FIG. 2B and FIGS. 3A to 3C, for convenience of description, it is described that the nostril is covered with the portion b and the mouth is covered with the portion e, but both the nostril and the mouth may be covered only with the portion e.

In FIG. 2B and FIGS. 3A to 3C, the main body portion is equally divided into six portions for convenience of description, but such division is merely illustrated as an example, and for example, the division and ratio between the "piezoelectric region" and the "non-piezoelectric region" may be appropriately changed from the viewpoint of three-dimensionally molding the main body portion of the mask.

In the mask of the present disclosure, each of the "piezoelectric region" and the "non-piezoelectric region" of the main body portion preferably has a sheet-like structure. It is more preferable that the "piezoelectric region" and the "non-piezoelectric region" of the main body portion are coupled to each other by stitching. In the main body portion, it is preferable that the "piezoelectric region" and the "non-piezoelectric region" are stitched in a state of overlapping each other and coupled to each other. When the "piezoelectric region" and the "non-piezoelectric region" are coupled to each other by stitching, the positions of the stitches or perforations are not particularly limited, and are not limited to, for example, the portion indicated by the solid line in FIGS. 3A to 3C. Furthermore, the position of the stitch may be appropriately changed and added from the viewpoint of, for example, three-dimensionally stitching the main body portion of the mask. For example, a stitch may be present at a central position so as to equally divide the main body portion into the left and right along the ridge of the nose in a direction perpendicular to the lip.

Hereinafter, the mask of the present disclosure will be described in more detail with reference to the first to sixth embodiments as preferred embodiments.

First Embodiment

Figure 4:
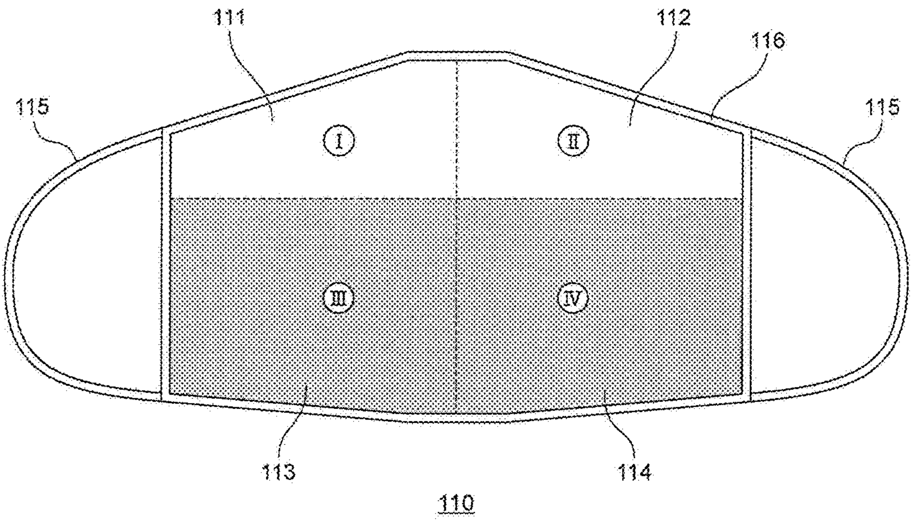
FIG. 4 is a schematic view schematically illustrating a mask according to a first embodiment of the present invention.

FIG. 4 schematically illustrates a mask 110 according to a first embodiment of the present invention. FIG. 4 is a front view or a plan view of the mask 110 as viewed from the front, and an outer shape, a dimension, an aspect ratio, and the like may be different from those of the actual device. In addition, the shape of the main body portion of the mask, particularly the outer shape of the main body portion is not limited to the illustrated shape, and may be, for example, a rectangle as illustrated in FIG. 3 or another shape (for example, polygonal shapes such as a hexagonal shape, a heptagonal shape, and an octagonal shape).

The main body portion of the mask 110 illustrated in FIG. 4 is formally divided into four portions (111, 112, 113, and 114), with the portions 111 and 112 constituting a "non-piezoelectric region" (I and II) and the portions 113 and 114 constituting a "piezoelectric region" (III and IV).

The main body portion of the mask 110 illustrated in FIG. 4 has a structure in which the non-piezoelectric region (I and II) is disposed in two portions (111 and 112) of the "upper half", and the piezoelectric region (III and IV) is disposed in two portions (113 and 114) of the "lower half".

In the main body portion of the mask 110 illustrated in FIG. 4, the "non-piezoelectric region" (I and II) and the "piezoelectric regions" (III and IV) are disposed in the "upper half" and the "lower half", respectively, so that the mask 110 illustrated in FIG. 4 can correspond to the aspect illustrated in FIG. 3A. However, the mask 110 illustrated in FIG. 4 is different from the mode schematically illustrated in FIG. 3A in that the main body portion is divided into four portions (111, 112, 113, and 114). In addition, two broken lines in the vertical and horizontal directions illustrated in FIG. 4 indicate boundaries of four portions (111, 112, 113, and 114), and may indicate stitches that can be formed when the four portions are stitched together.

The "non-piezoelectric region" (I and II) preferably has relatively lower elasticity than that of the piezoelectric region (III and IV), is relatively less likely to extend or are hard, and is formed of a woven fabric, a knitted fabric (particularly, tricot), or the like.

The "piezoelectric region" (III and IV) preferably has relatively higher elasticity than that of the non-piezoelectric region (I and II), is relatively easy to extend or has flexibility, and is preferably formed of a knitted fabric (particularly a knit), a nonwoven fabric, or the like.

The "ear hooking portion" (115) is preferably stitched to the main body portion, and is preferably formed of cloth (woven fabric, knitted fabric, nonwoven fabric, and the like) and a string (strings made of yarn, leather, rubber, and the like, and the like).

The "edge portion" (116) may or may not be present and is preferably made of cloth (woven fabric, knitted fabric, nonwoven fabric, and the like). The edge portion may be made of a binder tape, microfiber cloth, or the like. In addition, a material such as a rubber material generally used for preventing slippage for clothing, an adhesive generally used for an adhesive plaster or a medical dressing, or a cloth-like high friction material that can be produced from NANOFRONT (registered trademark) manufactured by TEIJIN FRONTIER Co., Ltd. may be disposed at a portion (or skin side) where the material can come into contact with the skin. Furthermore, a metal or resin wire or the like may be disposed or embedded in a portion of the edge portion that can be in contact with the tip of the nose or the ridge of the nose. Such a wire may have flexibility or may be deformable according to the unevenness of the face.

In the mask 110 according to the first embodiment of the present invention illustrated in FIG. 4, since the non-piezoelectric region (I and II) of the main body portion has relatively lower elasticity than that of the piezoelectric region (III and IV), the non-piezoelectric region (I and II) is relatively less likely to expand and contract than that the piezoelectric region (III and IV), and can relatively expand and contract with an external force concentrated on the piezoelectric region (III and IV).

Since the piezoelectric region (III and IV) mainly cover the mouth (refer to FIG. 2B), for example, the piezoelectric region (III and IV) can be contracted more intensively in the vertical direction (or the longitudinal direction) according to opening and closing of the mouth during utterance, chewing of food such as gum, and physiological phenomena such as yawning and sneezing. Here, since the piezoelectric region can intensively generate an electric field and/or a potential (or a charge) in the "vertical direction" (longitudinal direction) by such contraction, actions of antibacterial property and/or antiviral property can be exerted by focusing more on the mouth area.

Second Embodiment

Figure 5:
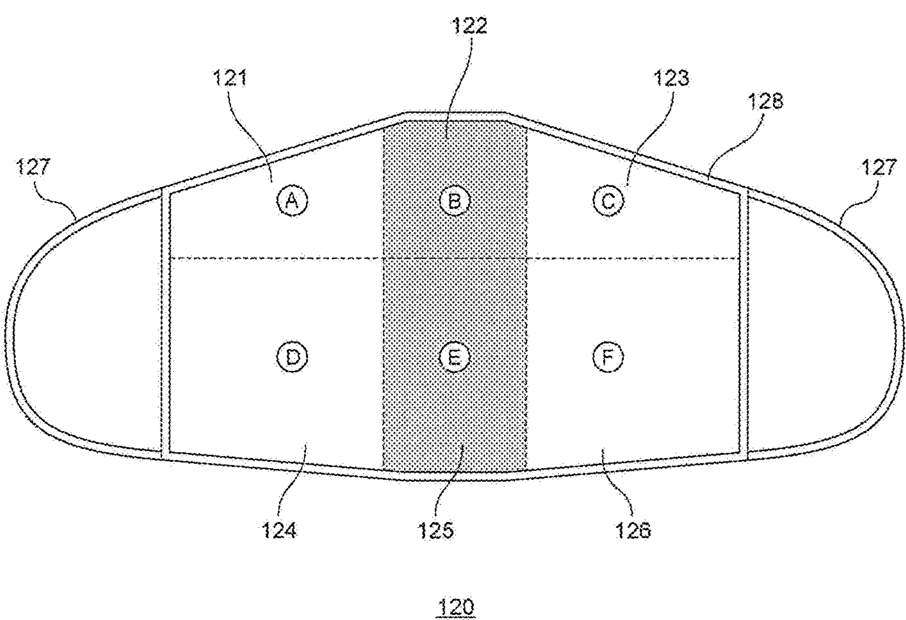
FIG. 5 is a schematic view schematically illustrating a mask according to a second embodiment of the present invention.

FIG. 5 schematically illustrates a mask 120 according to a second embodiment of the present invention. The main body portion of the mask 120 illustrated in FIG. 5 is first formally divided into six portions (121, 122, 123, 124, 125, and 126), of which four portions 121, 123, 124, and 126 form a "non-piezoelectric region" (A, C, D, and F) and the remaining two portions 122 and 125 form a "piezoelectric region" (B and E). In other words, in the mask 120, the left non-piezoelectric region (A, D) and the right non-piezoelectric region (C, F) are respectively arranged in the left portion (121, 124) and the right portion (123, 126). That is, non-piezoelectric region is disposed on both left and right sides of the mask main body. The piezoelectric region (B, E) is disposed in a central portion (122, 125) of the mask main body. Therefore, the piezoelectric region (B, E) is disposed in a band shape in the vertical direction (or longitudinal direction) through the center of the main body portion.

The mask 120 illustrated in FIG. 5 can correspond to the aspect illustrated in FIG. 3B. Here, the broken lines illustrated in FIG. 5 each indicate a boundary of six portions (121 to 126), and may indicate a stitch that can be formed when the six portions are stitched together. Furthermore, the portions 122 and 125 may be further divided into left and right portions, respectively, and may have stitches in the vertical direction (longitudinal direction) at the centers of the portions 122 and 125 (not shown), for example, similarly to the aspect illustrated in FIG. 4.

For example, as illustrated in FIG. 5, the mask 120 of the second embodiment has stitches in both the vertical direction (longitudinal direction) and the horizontal direction (lateral direction), but the stitches in the horizontal direction (lateral direction) may be omitted. That is, the main body portion may be divided into three or more portions only in the longitudinal direction. In that case, only stitches in the vertical direction (longitudinal direction) may exist.

The stitches in the vertical direction (longitudinal direction) serve to three-dimensionally shape the mask main body and also serve to adjust the airflow in the vertical direction (longitudinal direction) along the ridge of the nose. As a result, a space is formed around the nostril and the mouth, and the difficulty in breathing can be reduced.

The stitches in the horizontal direction (lateral direction) serve to three-dimensionally shape the mask main body, and in particular can serve as ribs or wires that shape the mask main body to fit the face.

The "non-piezoelectric region" (left side A, D and right side C, F) preferably has relatively lower elasticity than that of the piezoelectric region (B, F), is relatively less likely to extend or are hard, and is formed of a woven fabric, a knitted fabric (particularly, tricot), or the like.

The "piezoelectric region" (B, E) preferably has relatively higher elasticity than that of the non-piezoelectric region (left side A, D and right side C, F), is relatively easy to extend or has flexibility, and is preferably formed of a knitted fabric (particularly a knit), a nonwoven fabric, or the like.

As the "ear hooking portion" (127) and the "edge portion" (128), the same ones as the ear hooking portion 115 and the edge portion 116 of the aspect illustrated in FIG. 4 can be used.

In the mask 120 according to the second embodiment of the present invention illustrated in FIG. 5, an external force is concentrated on a central piezoelectric region (B, E), and the piezoelectric region can relatively expand and contract.

Since the central piezoelectric region (B, E) covers both the nostril and the mouth (refer to FIG. 2B), for example, the piezoelectric region (B, E) can be contracted in the "vertical direction" according to opening and closing of the mouth during utterance, chewing of food such as gum, and physiological phenomena such as yawning and sneezing. Here, since the central piezoelectric region (B, E) can intensively generate an electric field and/or a potential (or charge) by such contraction, actions of the antibacterial property and/or antiviral property can be exerted by focusing on both of the nostril and the mouth area.

Further, in the mask 120, since both left and right sides of the main body portion can be relatively fixed by the non-piezoelectric region (left side A, D and right side C, F), the piezoelectric region (B, E) at the center can expand and contract not only in the "vertical direction" (longitudinal direction) but also in the "horizontal direction" (lateral direction), and the expansion and contraction can be further concentrated on the piezoelectric region (B, E) at the center. The generated potential can then be further increased, and thus the generation of electric field and/or potential (or charge) can be increased or maximized. In addition, the presence of the stitches in the horizontal direction (lateral direction) allows the main body portion of the mask 120 to be formed into cells (can be divided into at least 6 cells). In particular, in the region E, the main body portion can be contracted in the vertical direction (longitudinal direction) to intensively generate electric potential, in particular, to the sub-nose and the mouth area which are air passages, and thus, in the region E, the effects such as antibacterial property and/or antiviral property can be improved.

Figure 6:
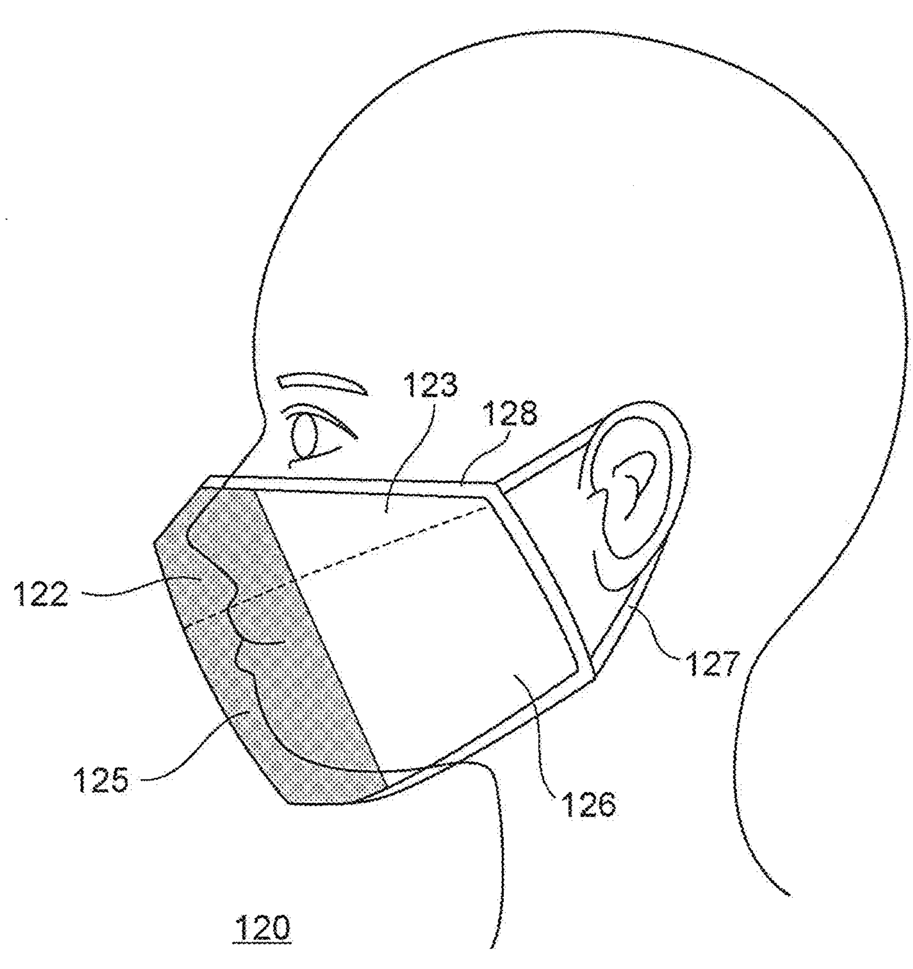
FIG. 6 is a schematic view schematically illustrating a state in which the mask according to the second embodiment of the present invention is worn on a face.

FIG. 6 schematically illustrates a state in which the mask 120 according to the second embodiment of the present invention is worn on a face.

Third Embodiment

Figure 7:
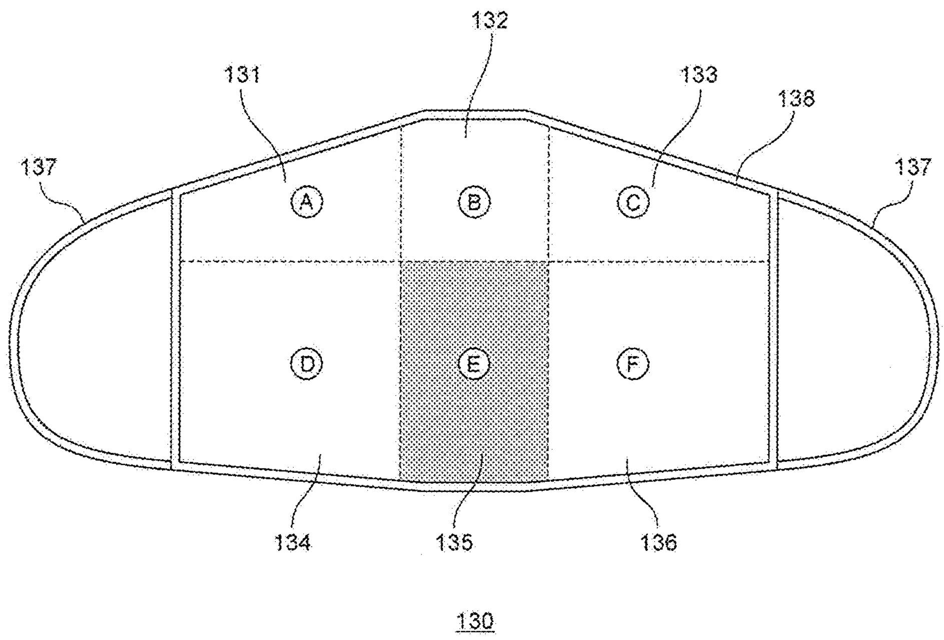
FIG. 7 is a schematic view schematically illustrating a mask according to a third embodiment of the present invention.

FIG. 7 schematically illustrates a mask 130 according to a third embodiment of the present invention. The main body portion of the mask 130 illustrated in FIG. 7 is divided into six portions (131, 132, 133, 134, 135, and 136) similarly to the mask 120 illustrated in FIG. 5, for example, and five portions 131, 132, 133, 134, and 136 form a "non-piezoelectric region" (A, B, C, D, and F), and only the remaining one portion 135 forms a "piezoelectric region" (E). In other words, in the mask 130, the "piezoelectric region" (E) is disposed in the "central portion of the lower half" (135) of the main body portion, and the non-piezoelectric region (D, A, B, C, and F) is disposed in portions (134, 131, 132, 133, and 136) in the periphery the "piezoelectric region" (E).

The mask 130 illustrated in FIG. 7 can correspond to the aspect illustrated in FIG. 3C. It can also be said that the mask 130 illustrated in FIG. 7 is obtained by changing the region B in the mask 120 illustrated in FIG. 5 from the "piezoelectric region" to the "non-piezoelectric region". Therefore, other configurations of the mask 130 illustrated in FIG. 7 may be similar to those illustrated in FIG. 5.

In the mask 130 according to the third embodiment of the present invention illustrated in FIG. 7, the external force is concentrated only on the "piezoelectric region" (E) of the "central portion of the lower half" (135), and the mask can relatively expand and contract.

Since the "piezoelectric region" (E) of the central portion (135) of the lower half of the main body portion mainly covers the mouth (refer to FIG. 2B), for example, only the piezoelectric region (E) can be contracted in the "vertical direction" (longitudinal direction) according to opening and closing of the mouth during utterance, chewing of food such as gum, and physiological phenomena such as yawning and sneezing. Here, since the piezoelectric region (E) can intensively generate an electric field and/or a potential (or charge) by such contraction, an action such as further improved antibacterial property and/or antiviral property can be exerted by focusing, particularly, on the mouth area.

Furthermore, in the mask 130, since the periphery of the piezoelectric region (E) is surrounded by the non-piezoelectric region (D, A, B, C, and F) and relatively fixed, only the piezoelectric region (E) can expand and contract not only in the "vertical direction" (longitudinal direction) but also in the "horizontal direction" (lateral direction), and an external force can be further concentrated in the piezoelectric region (E). Therefore, the generated electric field and/or potential (or charge) can be further increased, and the generation of the electric field and/or potential (or charge) can be maximized.

Fourth Embodiment

Figure 8:
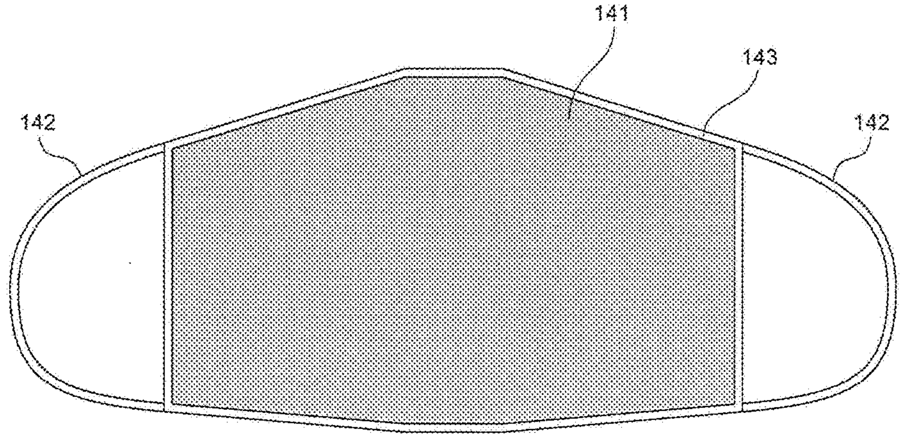
FIG. 8 is a schematic view schematically illustrating a mask according to a fourth embodiment of the present invention.

FIG. 8 schematically illustrates a mask 140 according to a fourth embodiment of the present invention. In the mask 140 illustrated in FIG. 8, the entire surface of the main body portion includes a piezoelectric portion 141, that is, the entire surface of the main body portion is a "piezoelectric region", and further has an "edge portion" (143) as essential constituent requirements.

As the "ear hooking portion" (142), the same ones as the ear hooking portion 115 of the aspect illustrated in FIG. 4 can be used.

The "edge portion" (143) is made of cloth (woven fabric, knitted fabric, nonwoven fabric, and the like), and is preferably made of a binder tape, microfiber cloth, or the like having high adhesion to the skin. Such an "edge portion" (143) can suppress the mask from being displaced from the face when the mask is worn, and can minimize loss of external force applied to the mask main body. As a result, even in a case where the external force is minute, an electric field and/or a potential (or a charge) can be generated in the piezoelectric portion (piezoelectric region) 141, and the piezoelectric effect (electric field, potential, electric field and/or charge, or the like) can be maximized. In order to suppress the mask from being displaced from the face, a material such as a rubber material generally used for preventing slippage for clothing, an adhesive generally used for an adhesive plaster or a medical dressing, or a cloth-like high friction material that can be produced from NANOFRONT (registered trademark) manufactured by TEIJIN FRONTIER Co., Ltd. may be disposed at a portion (or skin side) where the material can come into contact with the skin. Furthermore, in order to make deviation of the mask less likely to occur, a metal or resin wire or the like may be disposed or embedded in a portion of the edge portion that can be in contact with the tip of the nose or the ridge of the nose. Such a wire may have flexibility or may be deformable according to the unevenness of the face.

Figure 9:
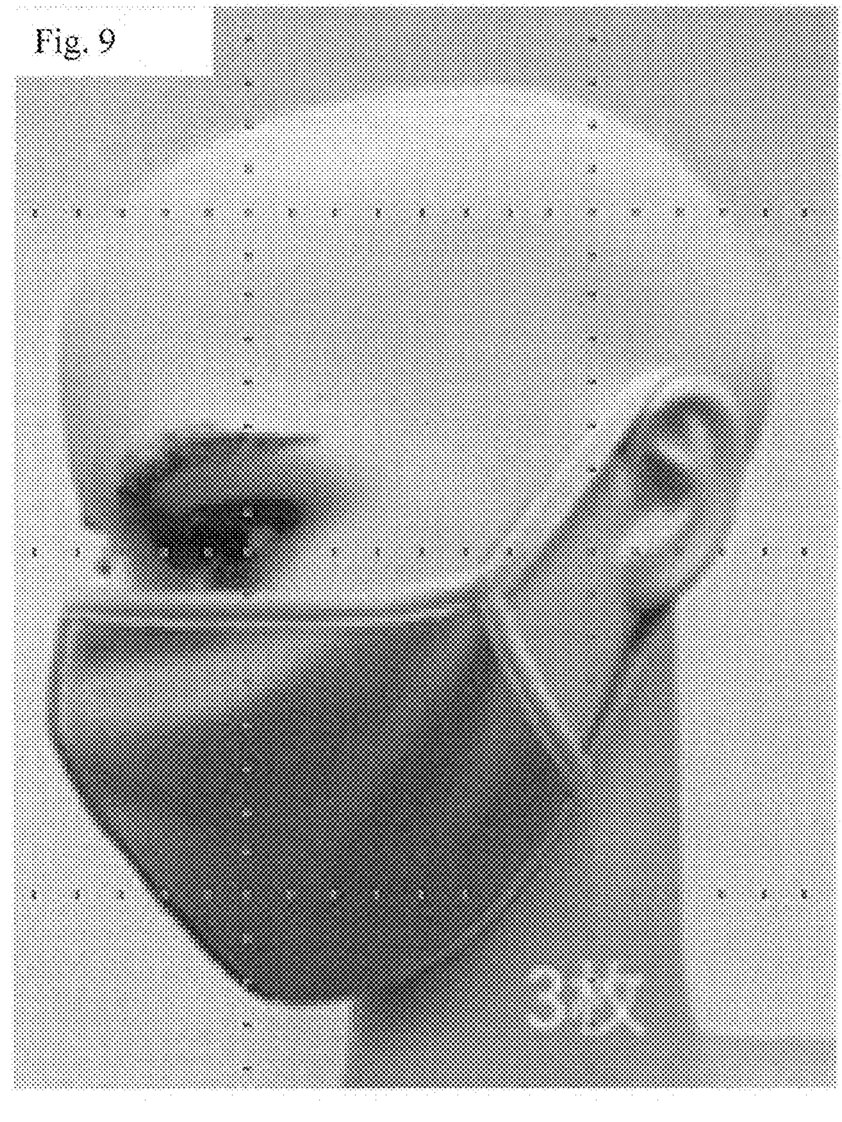
FIG. 9 is a photograph illustrating a state in which the mask according to the fourth embodiment of the present invention is worn on a face.

In the mask 140 according to the fourth embodiment of the present invention illustrated in FIG. 8, the main body portion may be changed to, for example, those in the aspects illustrated in FIGS. 3A, 3B, 3C, 4, 5, and 7. Furthermore, in the mask 140, for example, as illustrated in FIG. 4, stitches may be provided in the vertical direction (or longitudinal direction) at the center of the main body portion. That is, in the mask 140, the main body portion may be divided into left and right portions and coupled to each other by stitching (refer to FIG. 9).

Fifth Embodiment

Figure 10:
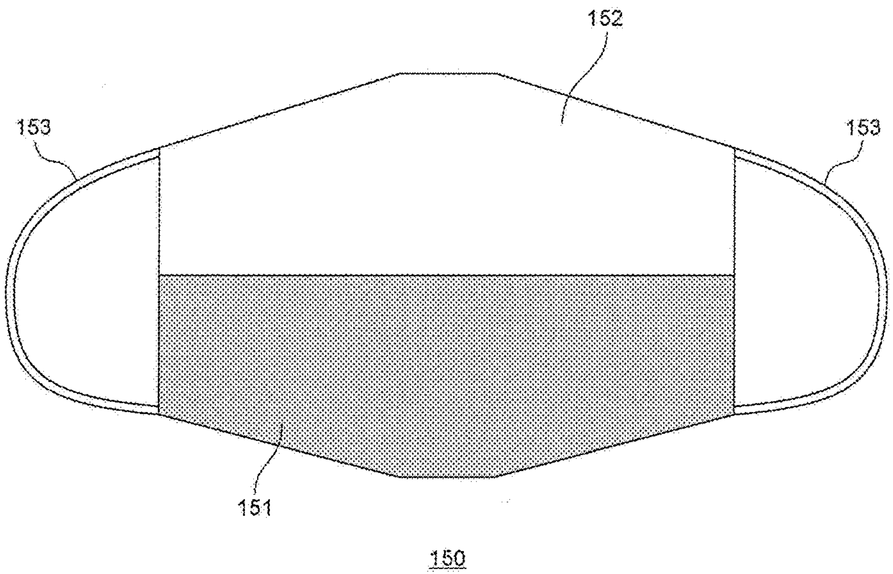
FIG. 10 is a schematic view schematically illustrating a mask according to a fifth embodiment of the present invention.

FIG. 10 schematically illustrates a mask 150 according to a fifth embodiment of the present invention. In the main body portion of the mask 150, an upper portion 152 (upper half) is a non-piezoelectric region, a lower portion 151 (lower half) is a piezoelectric region, and the portion 151 includes a sheet-like piezoelectric portion.

The non-piezoelectric region of the upper half may be formed in a cup shape, for example, and is preferably harder than the piezoelectric region of the lower half. It is preferable that the non-piezoelectric region of the upper half of the main body portion has substantially no elasticity. The piezoelectric region of the lower half of the main body portion is preferably coupled to the non-piezoelectric region of the upper half in a pulled state, that is, in a tensioned state, for example. Here, the manner of coupling is not particularly limited, and for example, the coupling can be performed by stitching, adhesion, fusion, or the like. In such a state, an electric field and/or a potential (or a charge) can be generated only by applying a slight vibration or a fine vibration to the piezoelectric region of the lower half, and the piezoelectric effect (electric field, potential, electric field and/or charge, or the like) can be maximized.

Sixth Embodiment

Figure 11:
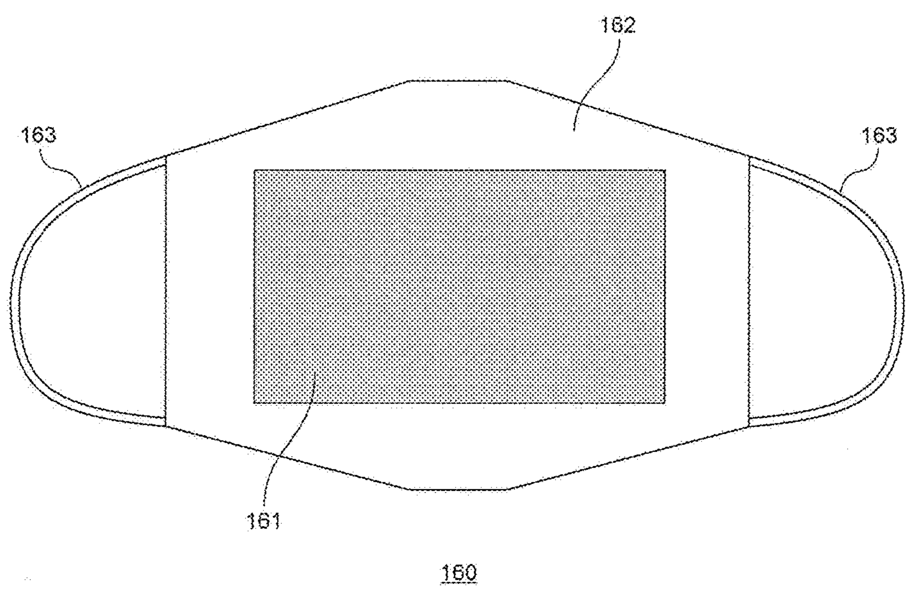
FIG. 11 is a schematic view schematically illustrating a mask according to a sixth embodiment of the present invention.

FIG. 11 schematically illustrates a mask 160 according to a sixth embodiment of the present invention. The configuration of the mask 160 is basically similar to that illustrated in FIG. 10, and in the main body portion of the mask 160, it is preferable that a peripheral portion 162 (outer peripheral portion) is a non-piezoelectric region, a central portion 161 (central portion) is a piezoelectric region, and the portion 161 is constituted by a sheet-like piezoelectric portion. Even in such an aspect, an electric field and/or a potential (or a charge) can be generated in the central portion only by applying a slight vibration or a fine vibration to the piezoelectric region of the central portion, and the piezoelectric effect (electric field, potential, electric field and/or charge, or the like) can be maximized.

[Multilayering]

The main body portion of the mask of the present disclosure may be multilayered as necessary. In the mask of the present disclosure, for example, two or more of the above-described main body portions may be used in an overlapping manner. At this time, the main body portions to be used may be the same or different. Specifically, the main body portions of the masks illustrated in FIGS. 4 to 8 may be appropriately combined and used in an overlapping manner as necessary.

When three or more main body portions of the present disclosure are used in an overlapping manner, for example, other filter layers such as an electret filter, a meltblown nonwoven fabric filter, and a nanofilter (filter including fibers having a diameter of nano order) may be provided. As such a filter layer, for example, for the purpose of dust collection, it is preferable to select and use a filter layer having higher collection efficiency (for example, collection efficiency according to JIS B 9908) than the main body portion of the present disclosure.

When another filter layer such as an electret filter is provided, it is preferable that the two outermost layers (that is, the layer on the side in contact with the atmosphere and the layer on the side in contact with the face) are layers including the main body portion of the present disclosure.

Among the two outermost layers, the layer on the side in contact with the atmosphere may be a layer including the main body portion of the present disclosure, and the layer on the side in contact with the face may be a functional layer having another function.

Examples of the functional layer include a functional layer that imparts cooling sensitivity and thermal sensitivity. When the functional layer is formed of hygroscopic heat generating fibers, thermal sensitivity can be imparted to the functional layer. When the functional layer is formed of a fabric sheet containing a cooling agent such as menthol, salicylic acid, camphor, or peppermint oil, or a fiber having a contact cooling sensitivity function, the cooling sensitivity can be imparted to the functional layer.

[Air Permeability]

In the mask of the present disclosure, it is preferable to secure at least air permeability enough to allow breathing.

[Yarn Formed of Electric Field Forming Filament]

The "yarn formed of an electric field forming filament" (hereinafter, sometimes abbreviated as "yarn of the present disclosure" or simply "yarn") included in the "piezoelectric portion" that may constitute at least a part of the main body portion of the mask of the present disclosure will be described in detail below. Although the description will be made with reference to the drawings as necessary, various elements in the drawings are merely schematically and exemplarily shown for understanding of the present invention, and appearance, dimensional ratios, and the like may be different from the actual ones.

The yarn of the present disclosure includes an "electric field forming filament" (or a fiber capable of forming an electric field by surface charge), and for example, an electric field is formed by applying an external force in an axial direction of the yarn, and a positive or negative surface potential can be generated.

The various numerical ranges referred to herein are intended to include the lower and/or upper numerical limits themselves, unless otherwise stated. That is, when a numerical range such as 1 to 10 is taken as an example, it can be interpreted as including not only the lower limit value "1" but also the upper limit value "10".

Also, various numerical values may be labeled with "approximately" or "about", meaning that the terms "approximately" and "about" can include variations of a few percent, for example, ±10%, ±5%, ±3%, ±2%, and ±1%.

[Basic Configuration of Yarn]

The yarn of the present disclosure includes a plurality of "electric field forming filaments". The number of electric field forming filaments is not particularly limited, and for example, 2 or more, 2 to 500, preferably 10 to 350, and more preferably about 20 to 200 electric field forming filaments may be included in the yarn of the present disclosure.

In the present disclosure, the "electric field forming filament" basically means "fiber (filament) capable of generating a charge by energy from the outside to form a potential and/or an electric field" as described above (hereinafter, it may be referred to as "potential generating fiber", "potential generating filament", "electric field forming fiber", "charge generating fiber" or "charge generating filament"). As the electric field forming filament, for example, a charge generating fiber described in Japanese Patent No. 6428979 or the like may be used.

The dimension (length, thickness (diameter), and the like) and the shape (cross-sectional shape and the like) of the electric field forming filament are not particularly limited. The yarn of the present disclosure including such electric field forming filaments may include a plurality of electric field forming filaments having different thicknesses. Therefore, the yarn of the present disclosure may or may not have a constant diameter in the length direction.

The electric field forming filament may be a long fiber or a short fiber. The electric field forming filament may have a length (dimension) of, for example, 0.01 mm or more. The length may be appropriately selected according to a desired use.

The thickness (diameter) of the electric field forming filament is not particularly limited, and may be the same (constant) or may not be the same along the length of the electric field forming filament. The electric field forming filament may have a thickness of, for example, 0.001 μm (1 nm) to 1 mm. The thickness may be appropriately selected according to a desired use.

Furthermore, the fiber strength of the yarn of the present disclosure is preferably 1 to 5 cN/dtex. Thus, even if greater deformation occurs to generate a high potential, the yarn can withstand without breaking. The fiber strength is more preferably 2 to 10 cN/dtex, still more preferably 3 to 10 cN/dtex, and most preferably 3.5 to 10 cN/dtex. For the same purpose, the elongation of the yarn of the present disclosure is preferably 10% to 50%.

The shape of the electric field forming filament, particularly cross-sectional shape thereof is not particularly limited, and the electric field forming filament may have, for example, a circular, elliptical, rectangular, or irregular cross section. It is preferable to have a circular cross-sectional shape.

The electric field forming filament preferably includes, for example, a material (hereinafter, it may be referred to as a "piezoelectric material" or a "piezoelectric body") having a piezoelectric effect (polarization phenomenon by external force) or piezoelectricity (the property of generating a voltage when a mechanical strain is applied or, conversely, generating a mechanical strain when a voltage is applied). Among them, it is particularly preferable to use fibers containing a piezoelectric material (hereinafter, it may be referred to as a "piezoelectric fiber"). Since the piezoelectric fibers can form an electric field by piezoelectric, a power supply is unnecessary, and there is no risk of electric shock.

The life of the piezoelectric material contained in the piezoelectric fiber lasts longer than, for example, the antibacterial effect of a drug or the like. Such piezoelectric fibers are less likely to cause allergic reactions.

The "piezoelectric material" can be used without particular limitation as long as it is a material having a piezoelectric effect or piezoelectricity, and may be an inorganic material such as piezoelectric ceramics or an organic material such as a polymer.

The "piezoelectric material" (or "piezoelectric fiber") preferably contains a "piezoelectric polymer".

Examples of the "piezoelectric polymer" include a "piezoelectric polymer having pyroelectricity" and a "piezoelectric polymer having no pyroelectricity".

The "piezoelectric polymer having pyroelectricity" is generally meant a piezoelectric material formed of a polymeric material that has pyroelectricity and can also generate charges (or potentials) on the surface thereof simply by imparting a change in temperature. Examples of such a piezoelectric polymer include polyvinylidene fluoride (PVDF). In particular, one that can generate charges (or potentials) on the surface thereof by thermal energy of the human body is preferable.

The "piezoelectric polymer without pyroelectricity" generally means a piezoelectric polymer formed of a polymeric material and excluding the above-described "piezoelectric polymer with pyroelectricity". Examples of such a piezoelectric polymer include polylactic acid (PLA). As the polylactic acid, poly-L-lactic acid (PLLA) obtained by polymerizing an L-form monomer, poly-D-lactic acid (PDLA) obtained by polymerizing a D-form monomer, and the like are known.

The yarn of the present disclosure may have a configuration in which, as the electric field forming filament (or the charge generating fiber), a conductor is used as the core yarn, an insulator is wound (covered) around the conductor, and a voltage is applied to the conductor to generate a charge.

The yarn of the present disclosure may be a yarn obtained by simply aligning a plurality of electric field forming filaments (a paralleled yarn or a non-twisted yarn), may be a twisted yarn (a stranded yarn or a twisted yarn), may be a crimped yarn (a crimped yarn or a false-twisted yarn), or may be a spun yarn (a spun yarn).

The yarn stranding method, crimping method, and spinning method are not particularly limited, and known methods in the related art can be used.

For example, as illustrated in FIG. 12A, the yarn 1 can also be configured by stranding a plurality of electric field forming filaments 10. In the aspect illustrated in FIG. 12A, the yarn 1 is a left-twisted yarn (hereinafter, referred to as "S yarn") obtained by leftward twisting the electric field forming filament 10, but may be a right-twisted yarn (hereinafter, referred to as "Z yarn") obtained by rightward twisting the electric field forming filament 10 (refer to, for example, yarn 2 of FIG. 14A). Thus, the yarn of the present disclosure may be either an "S yarn" or a "Z yarn" in the case of the stranded yarn.

In the yarn of the present disclosure, the distance between the electric field forming filaments 10 is approximately 0 μm to approximately 10 μm, and generally about 5 μm. When the distance between the electric field forming filaments 10 is 0 μm, it means that the electric field forming filaments are in contact with each other.

Hereinafter, in order to describe the yarn of the present disclosure in detail, examples of the yarn of the present disclosure will be described in more detail with reference to FIGS. 12A to 14, taking an aspect as an example, in which a piezoelectric material is included as the electric field forming filament and the piezoelectric material is "polylactic acid".

Polylactic acid (PLA) that can be used as a piezoelectric material is a chiral polymer, and has a main chain with a spiral structure. Polylactic acid can exhibit piezoelectricity when molecules are uniaxially stretched and oriented. When a heat treatment is further performed to increase the crystallinity, the piezoelectric constant increases. By increasing the crystallinity as described above, the value of the surface potential can be improved.

The optical purity (Enantiomeric excess (e.e.)) of polylactic acid (PLA) can be calculated by the following equation:

$$\text{Optical purity }(\%)=\{|L\text{-form amount}-D\text{-form amount}|/(L\text{-form amount}+D\text{-form amount})\}\times 100$$

For example, in both of the D-form and the L-form, the optical purity is 90 wt % or more, preferably 95 wt % or more, more preferably 98 wt % to 100 wt %, still more preferably 99.0 wt % to 100 wt %, and particularly preferably 99.0 wt % to 99.8 wt %. As the L-form amount and the D-form amount of polylactic acid (PLA), for example, values obtained by a method using high performance liquid chromatography (HPLC) can be used.

As illustrated in FIG. 12A, the electric field forming filament (or piezoelectric fiber) 10 containing uniaxially stretched polylactic acid has tensor components of $d_{14}$ and $d_{25}$ as piezoelectric strain constants when a thickness direction is defined as a first axis, a stretching direction 900 is defined as a third axis, and a direction orthogonal to both the first axis and the third axis is defined as a second axis.

Therefore, polylactic acid can generate charges (or potential) most efficiently when distortion occurs in a direction of 45 degrees with respect to the uniaxially stretched direction.

The number average molecular weight (Mn) of the polylactic acid is, for example, $6.2\times10^4$, and the weight average molecular weight (Mw) is, for example, $1.5\times10^5$. The molecular weight is not limited to these values.

Figure 13A:
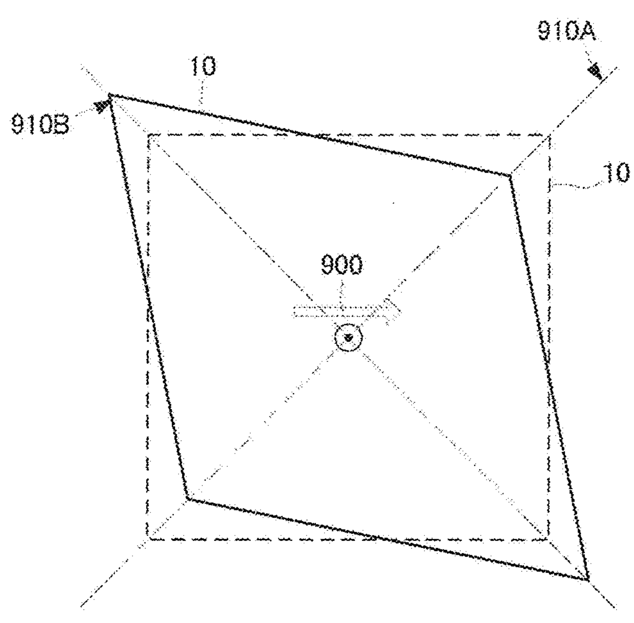
FIGS. 13A and 13B are diagrams illustrating a relationship among a uniaxial stretching direction of polylactic acid, an electric field direction, and deformation of an electric field forming filament (or piezoelectric fiber) 10.
Figure 13B:
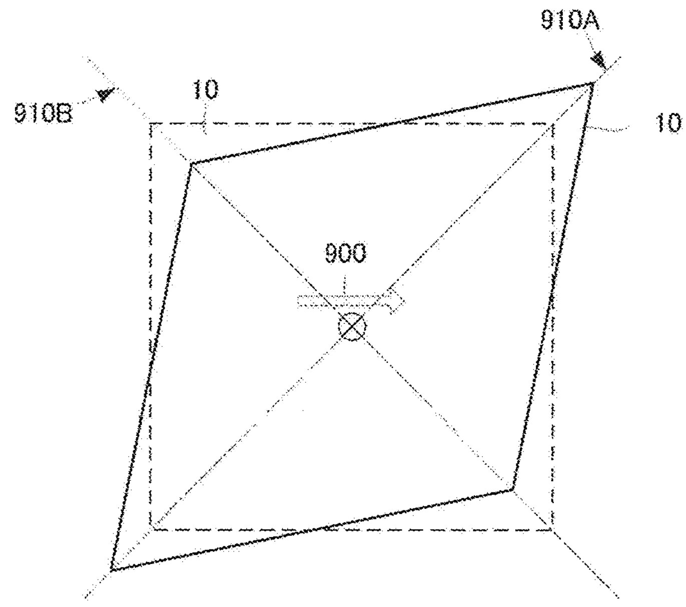

FIGS. 13A and 13B are diagrams illustrating a relationship among a uniaxial stretching direction of polylactic acid, an electric field direction, and deformation of an electric field forming filament (or piezoelectric fiber) 10.

As illustrated in FIG. 13A, when the electric field forming filament 10 contracts in the direction of the first diagonal line 910A and extends in the direction of the second diagonal line 910B orthogonal to the first diagonal line 910A, an electric field can be generated in a direction from the back side to the front side of the paper surface. That is, the electric field forming filament 10 can generate a negative charge on the front side of the paper surface. As illustrated in FIG. 13B, the electric field forming filament 10 can generate a charge (or potential) even when extending in the direction of the first diagonal line 910A and contracting in the direction of the second diagonal line 910B, but the polarity is reversed, and an electric field can be generated in a direction from the surface to the back side of the paper surface. That is, the electric field forming filament 10 can generate a positive charge on the front side of the paper surface.

Polylactic acid may have piezoelectricity due to a molecular orientation treatment by stretching, and thus does not need to be subjected to a poling treatment unlike other piezoelectric polymers such as polyvinylidene fluoride (PVDF) or piezoelectric ceramics. The piezoelectric constant of uniaxially stretched polylactic acid is about 5 to 30 pC/N, and has a very high piezoelectric constant among polymers. Furthermore, the piezoelectric constant of polylactic acid does not vary with time and is extremely stable.

The electric field forming filament 10 is preferably a fiber having a circular cross section. The electric field forming filament 10 can be manufactured by, for example, a method in which a piezoelectric polymer is extruded and molded into a fiber, a method in which a piezoelectric polymer is melt-spun into a fiber (examples thereof include a spinning/stretching method in which a spinning step and a stretching step are separately performed, a straight stretching method in which a spinning step and a stretching step are connected, a POY-DTY method in which a false twisting step can also be performed at the same time, and an ultrahigh speed spinning method in which speed is increased), a method in which a piezoelectric polymer is formed into a fiber by dry or wet spinning (examples thereof include a phase separation method or a dry-wet spinning method in which a polymer as a raw material is dissolved in a solvent and extruded from a nozzle to form fibers, a gel spinning method in which fibers are uniformly formed into a gel while containing a solvent, and a liquid crystal spinning method in which fibers are formed using a liquid crystal solution or a melt), a method in which a piezoelectric polymer is formed into a fiber by electrostatic spinning, or the like. The cross-sectional shape of the electric field forming filament 10 is not limited to a circular shape.

For example, the yarn 1 illustrated in FIGS. 12A to 12C may be a yarn (multifilament yarn) (S yarn) obtained by twisting a plurality of electric field forming filaments 10 containing such polylactic acid (the way of twisting is not particularly limited). The stretching direction 900 of each electric field forming filament 10 coincides with the axial direction of the respective electric field forming filaments 10. Therefore, the stretching direction 900 of the electric field forming filament 10 is inclined to the left with respect to the axial direction of the yarn 1. The angle depends on the number of twists.

When, for example, tension (preferably tension in the axial direction) or stress (preferably tensile stress in the axial direction) is applied to the yarn 1, which is such an S yarn, as an "external force", a negative (−) charge (or potential) is generated on the surface of the yarn 1, and a positive (+) charge (or potential) can be generated on the inner side thereof The yarn 1 can form an electric field by a potential difference that can be generated by the electric charge. This electric field can also leak into a space in the vicinity to form a coupled electric field with other portions. Furthermore, the potential generated in the yarn 1 can also generate an electric field between the yarn 1 and an object when brought close to the object having a predetermined potential, for example, a predetermined potential (including a ground potential) such as a human body.

Figures 14A, 14B, 14C:
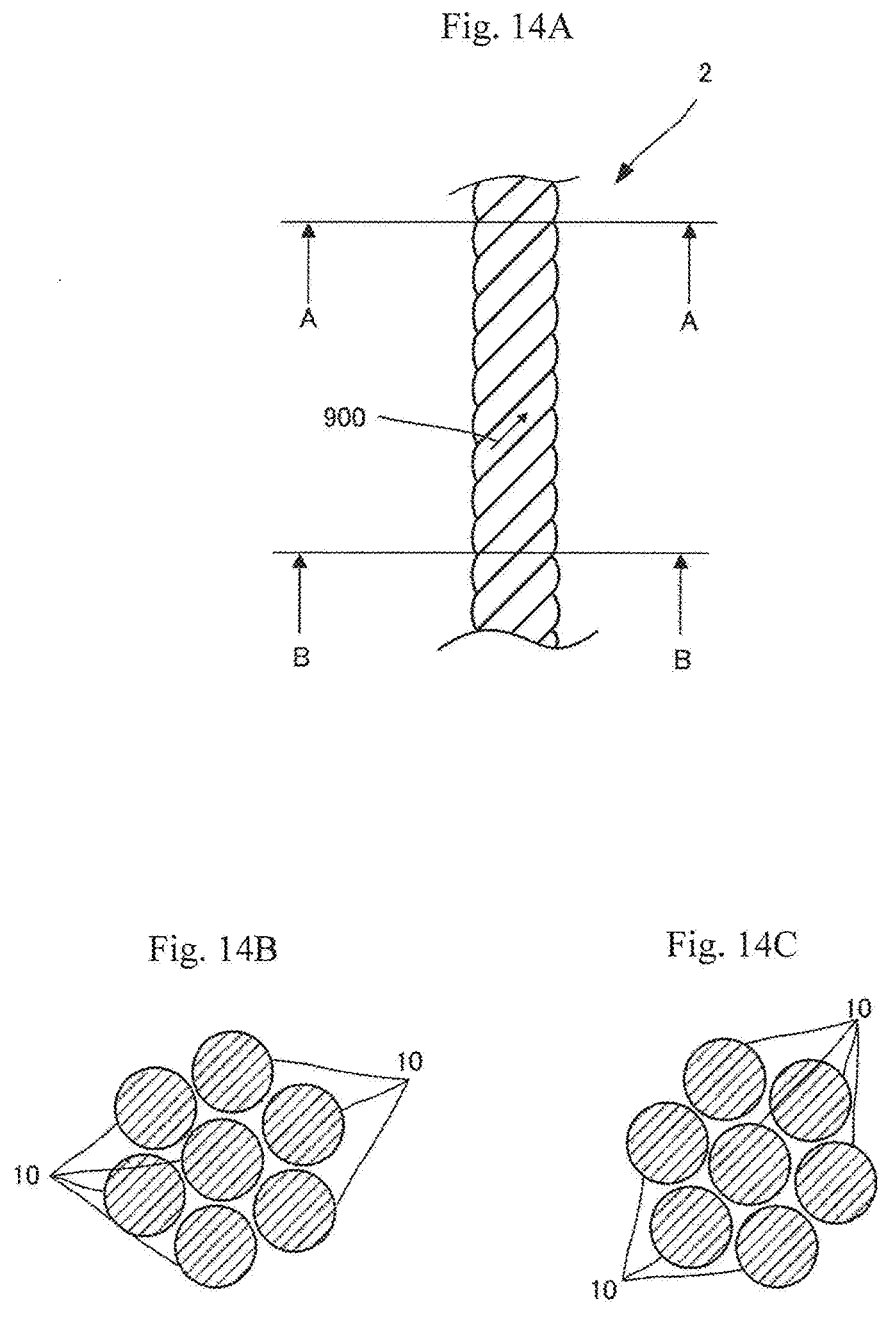

Next, referring to FIGS. 14A to 14C, since the yarn 2 is a Z yarn, the stretching direction 900 of the electric field forming filament (or piezoelectric fiber) 10 is inclined to the right with respect to the axial direction of the yarn 2. The angle depends on the number of twists of the yarn.

When, for example, tension (preferably tension in the axial direction) or stress (preferably tensile stress in the axial direction) is applied to the yarn 2, which is such a Z yarn, as an "external force", a positive (+) charge (or potential) is generated on the surface of the yarn 2, and a negative (−) charge (or potential) can be generated on the inner side thereof The yarn 2 can also form an electric field by a potential difference that can be generated by the electric charge. This electric field can also leak into a space in the vicinity to form a coupled electric field with other portions. Furthermore, the potential generated in the yarn 2 can also generate an electric field between the yarn 2 and an object when brought close to the object having a predetermined potential, for example, a predetermined potential (including a ground potential) such as a human body.

Furthermore, when the yarn 1 that is the S yarn and the yarn 2 that is the Z yarn are brought close to each other, an electric field can be generated between the yarn 1 and the yarn 2.

The polarities of charges (or potentials) generated in the yarn 1 and the yarn 2 are different from each other. The potential difference at each position can be defined by an electric field coupling circuit that can be formed by intricately entangling fibers, or a circuit that can be formed by a current path that can be accidentally formed in the yarn with moisture or the like.

The yarn 1 and the yarn 2 can be understood more deeply by reading Japanese Patent No. 6428979. Japanese Patent No. 6428979 is incorporated herein by reference.

In the yarn of the present disclosure, the electric field forming filament is preferably formed of polylactic acid (PLA). When the electric field forming filament contains a piezoelectric material such as polylactic acid, the surface potential can be more appropriately controlled. In addition, since the polylactic acid is hydrophobic, it is possible to provide a smooth touch to the piezoelectric portion and to impart comfort to the mask.

The crystallinity of "polylactic acid" is preferably within a range of 15% to 80%, for example. Within such a range, the piezoelectricity derived from the polylactic acid crystal is increased, and polarization due to the piezoelectricity of the polylactic acid can be more effectively generated.

The yarns of the present disclosure should not be construed as limited to the yarns that can be formed of the above aspects, particularly polylactic acid. The method for manufacturing the yarn of the present disclosure is also not particularly limited, and is not limited to the above manufacturing method.

Furthermore, the yarn of the present disclosure may be provided with a "dielectric" around the electric field forming filament. For example, as schematically illustrated in the sectional view of FIG. 15, a dielectric 100 may be provided around the electric field forming filament (or piezoelectric fiber) 10.

In the present disclosure, the term "dielectric" means a material or a substance having "dielectric properties" (a property of electrically polarizing (or dielectric polarization or electric polarization) positively and negatively by an electric field), and charges can be accumulated on a surface thereof.

The dielectric may be present in the longitudinal axis direction and the circumferential direction of the electric field forming filament, and may completely or partially cover the electric field forming filament. When the dielectric partially covers the electric field forming filament, the electric field forming filament itself may be exposed as it is in the uncovered portion.

Therefore, the dielectric may be provided entirely or partially in the longitudinal axis direction of the electric field forming filament. In addition, the dielectric may be provided entirely or partially in the circumferential direction of the electric field forming filament.

Figure 15:
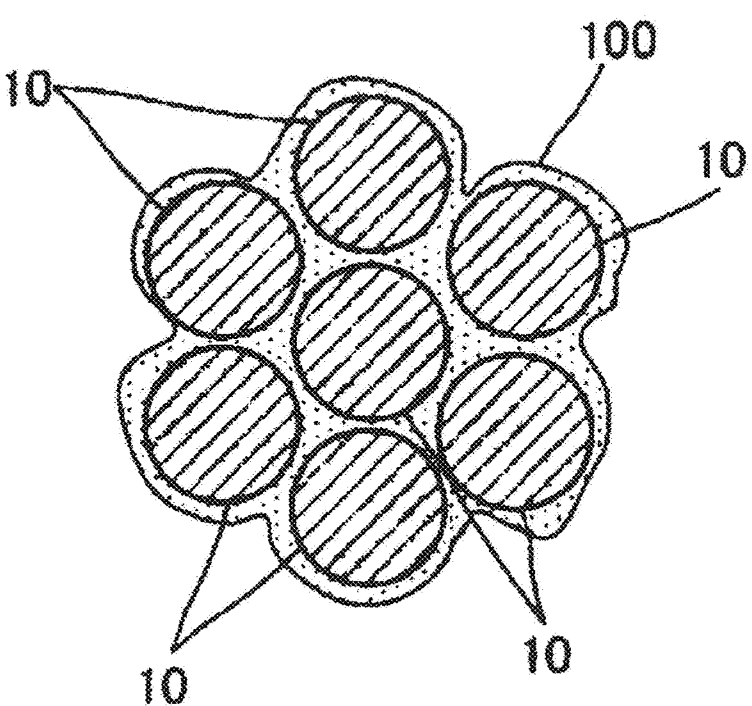
FIG. 15 is a sectional view schematically illustrating a cross section of a yarn including a dielectric 100 around an electric field forming filament 10.

In addition, the dielectric may have a uniform or non-uniform thickness (refer to, for example, FIG. 15).

The dielectric may be present between the plurality of electric field forming filaments, and in this case, there may be portions where no dielectric is present between the plurality of electric field forming filaments. In addition, bubbles or cavities may be present in the dielectric.

The dielectric is not particularly limited as long as it contains a dielectric material or substance. As the dielectric, a dielectric material (for example, an oil agent, an antistatic agent, and the like) known to be able to be used mainly as a surface treatment agent (or a fiber treatment agent) in the fiber industry may be used.

In the yarn of the present disclosure, the dielectric preferably contains an oil agent. As the oil agent, an oil agent (yarn making oil agent) used as a surface treatment agent (or fiber treatment agent) that can be used in the production of the electric field forming filament can be used (for example, anionic, cationic or nonionic surfactants, and the like). In addition, an oil agent (for example, anionic, cationic or nonionic surfactants, and the like) used as a surface treatment agent (or fiber treatment agent) that can be used in the step of manufacturing cloth (for example, knitting, weaving, and the like), and an oil agent (for example, anionic, cationic or nonionic surfactants, and the like) used as a surface treatment agent (or fiber treatment agent) that can be used in the finishing step can also be used. Here, as a representative example, a filament production step, a cloth production step, a finishing step, and the like have been described, but the present invention is not limited to these steps. As the oil agent, it is preferable to use, in particular, an oil agent used for reducing friction of the electric field forming filament.

Examples of the oil agent include DELION series manufactured by TAKEMOTO OIL & FAT CO., LTD., MARPOZOL series and MARPOZIES series manufactured by Matsumoto Yushi-Seiyaku Co., Ltd., and PARATEX series manufactured by MARUBISHI OIL CHEMICAL CO., LTD.

The oil agent may be present entirely or at least partially along the electric field forming filament. In addition, after the electric field forming filament is processed into a yarn, at least a part or all of the oil agent may fall off from the electric field forming filament by washing.

In addition, the dielectric used for reducing friction of the electric field forming filament may be a surfactant such as a detergent or a softener used during washing.

Examples of the detergent include ATTACK (registered trademark) series manufactured by Kao Corporation, TOP (registered trademark) series manufactured by Lion Corporation, and ARIEL (registered trademark) series manufactured by The P&G Japan Limited.

Examples of the softener include HAMMING (registered trademark) series manufactured by Kao Corporation, SOFLAN (registered trademark) series manufactured by Lion Corporation, and LENORE (registered trademark) series manufactured by The P&G Japan Limited.

The dielectric may have conductivity (property of passing electricity), and in this case, the dielectric preferably contains an antistatic agent. As the antistatic agent, an antistatic agent used as a surface treatment agent (or a fiber treatment agent) that can be used in the production of the electric field forming filament can be used. As the antistatic agent, it is preferable to use an antistatic agent used particularly for reducing the loosening of the electric field forming filament.

Examples of the antistatic agent include CAPRON series manufactured by NISSIN KAGAKU KENKYUSHO CO., LTD., NICEPOLE series and DEATRON series manufactured by NICCA CHEMICAL CO., LTD., and the like.

The antistatic agent may be present entirely or at least partially along the electric field forming filament. In addition, after the electric field forming filament is processed into a yarn, at least a part or all of the antistatic agent may fall off from the electric field forming filament by washing.

In addition, a surface treatment agent (or a fiber treatment agent) such as the above-described oil agent or antistatic agent, a detergent, a softener, and the like may not be present around the electric field forming filament. That is, the electric field forming filament and thus the yarn of the present disclosure may not contain a surface treatment agent (or a fiber treatment agent) such as the above-described oil agent and antistatic agent, a detergent, a softener, and the like. In that case, the air (or air layer) present between the electric field forming filaments may function as a dielectric. Therefore, in this case, the dielectric contains air.

For example, yarns containing no surface treatment agent (or fiber treatment agent), detergent, softener, or the like may be used by treating yarns with the surface treatment agent (or fiber treatment agent) such as the above-described oil agent or antistatic agent, detergent, softener, or the like attached around the electric field forming filament by washing or solvent immersion. In that case, the pure electric field forming filament will be exposed. Alternatively, in the present invention, a yarn containing only a pure electric field forming filament may be used.

Furthermore, in the present invention, for example, a yarn in which a surface treatment agent (or fiber treatment agent) such as the above-described oil agent or antistatic agent, detergent, softener, and the like are partially removed by a treatment such as washing or solvent immersion, and a pure electric field forming filament is partially exposed may be used.

The thickness of the dielectric (or the distance between the electric field forming filaments) is approximately 0 μm to approximately 10 μm, preferably approximately 0.5 μm to approximately 10 μm, more preferably approximately 2.0 μm to approximately 10 μm, and generally about 5 μm.

(Surface Potential)

In the yarn of the present disclosure, the surface potential generated by the application of the external force is, for example, 0.1 V or more, preferably 1.0 V or more (both positive and negative potentials can be generated). When the surface potential is 1.0 V or more, in the mask of the present disclosure, an antibacterial action, an antiviral action, and the like can be exhibited by the generated potential together with the dust collection force. Here, the method for measuring the surface potential is not particularly limited, and the surface potential can be measured using, for example, a scanning probe microscope.

The antibacterial action and the antiviral action may be a direct bactericidal action or a virucidal action by surface potential, or may be an action caused by generating a potential opposite to the potential of bacteria or viruses such as bacteria and fungi so as not to attract bacteria or viruses.

[Function of Mask of Present Disclosure]

The mask of the present disclosure can have functions such as antibacterial property and/or antiviral property in addition to dust-proof property. As described above, the function such as the antibacterial property and/or the antiviral property is mainly caused by the electric field and/or the potential (or the charge) generated by the expansion and contraction of the piezoelectric portion, particularly the piezoelectric region, included in the main body portion of the mask of the present disclosure. For example, due to the fact that the elasticity of the non-piezoelectric region excluding the piezoelectric region that can be included in the main body portion of the mask of the present disclosure is relatively lower than the elasticity of the piezoelectric region, an electric field and/or a potential (or a charge) is concentrated and effectively generated in the piezoelectric region, and functions such as antibacterial property and/or antiviral property are remarkably improved.

Since the mask of the present disclosure does not use a drug such as an antibacterial agent or an antiviral agent at all, the mask can be used more safely.

The mask of the present disclosure can be repeatedly washed and used because there is no possibility that antibacterial property and/or antiviral property are lowered by washing or the like. That is, as long as the mask is not damaged, the effects such as antibacterial property and/or antiviral property are maintained semi-permanently.

The mask of the present disclosure can also exhibit a deodorizing effect in addition to effects such as antibacterial property and/or antiviral property. It is considered that such a deodorizing effect is caused by, for example, killing or reducing bacteria and fungi that cause malodor by concentrating and effectively generating an electric field and/or a potential (or a charge) in the piezoelectric region.

In the mask of the present disclosure, since the yarn constituting the piezoelectric region, particularly preferably the electric field forming filament is formed of a hydrophobic polylactic acid, the stuffy feeling can be reduced, and the comfortable feeling or texture can be provided to the mouth, nose, and the like. In addition, effects such as easy breathing, followability to the mouth, nose, and the like, and improved fit feeling can be obtained.

As described above, the mask of the present disclosure has higher safety, and is excellent in dust-proof property, antibacterial property and/or antiviral property, deodorizing property, comfort, followability, fitting feeling, and the like, and can be repeatedly used by washing. Therefore, the mask of the present disclosure can be used as a dustproof mask, an antibacterial mask, an antiviral mask, a medical mask, or the like.

DESCRIPTION OF REFERENCE SIGNS

1, 2: Yarn
10: Electric field forming filament
100: Dielectric
110, 120, 130, 140, 150, 160: Mask
X: Main body portion
Y, 115, 127, 137, 142, 153, 163: Ear hooking portion
Z, 116, 128, 138, 143: Edge portion
141: Piezoelectric portion (piezoelectric region)
113, 114, 122, 125, 135, 151, 161: Portion of piezoelectric region
111, 112, 121, 123, 124, 126: Portion of non-piezoelectric region
131, 132, 133, 134, 136, 152, 162: Portion of non-piezoelectric region
900: Stretching direction
910A: First diagonal line
910B: Second diagonal line

What is claimed is:

1. A mask for covering at least a nostril and a mouth of a wearer, the mask comprising:

a main body portion, wherein at least a part of the main body portion comprises a sheet-like piezoelectric portion, and wherein the sheet-like piezoelectric portion includes a yarn having an electric field forming filament; and an ear hooking portion attached to the main body portion, wherein the main body portion of the mask further comprises: (i) a piezoelectric region that includes the sheet-like piezoelectric portion, and (ii) a non-piezoelectric region, and wherein a material of the piezoelectric region expands and contracts more than a material of the non-piezoelectric region, and wherein the piezoelectric region and the non-piezoelectric region are coupled to each other by stitching.

2. The mask according to claim 1, wherein the piezoelectric region is constructed to provide an antibacterial property and/or an antiviral property.

3. The mask according to claim 2, wherein the piezoelectric region is constructed to provide the antibacterial property and/or the antiviral property by expansion and contraction of the piezoelectric portion.

4. The mask according to claim 2, further comprising an edging portion along a periphery of the main body portion.

5. The mask according to claim 4, wherein the edging portion comprises a binder tape or a microfiber cloth.

6. The mask according to claim 4, wherein at least a part of the edging portion comprises a material having a greater friction against a skin of the wearer than a material of the main body portion.

7. The mask according to claim 4, further comprising a metal wire or a resin wire in a portion of the mask constructed to contact a tip or ridge of a nose of the wearer.

8. The mask according to claim 1, wherein the material of the piezoelectric region expands and contracts in a vertical direction and/or a horizontal direction.

9. The mask according to claim 1, wherein the piezoelectric region is positioned in a lower half of the main body portion.

10. The mask according to claim 1, wherein the piezoelectric region is positioned in a central portion of the main body portion.

11. The mask according to claim 1, wherein the piezoelectric region is positioned such that the piezoelectric region has a band shape in a vertical direction passing through a center of the main body portion.

12. The mask according to claim 1, wherein the piezoelectric region is positioned in a central portion of a lower half of the main body portion.

13. The mask according to claim 1, wherein the piezoelectric region comprises a knitted fabric or a stretchable woven or non-woven fabric of the yarn.

14. The mask according to claim 1 wherein the non-piezoelectric region comprises a woven fabric or a tricot.

15. The mask according to claim 1 wherein the non-piezoelectric region has a cup shape.

16. The mask according to claim 1, wherein the electric field forming filament comprises a polylactic acid.

* * * * *